United States Patent [19]

Krimmel

[11] 4,036,828
[45] July 19, 1977

[54] 3,4-BIS(4-SUBSTITUTED PIPERAZINYL)-3-CYCLOBUTENE-1,2-DIONES AND RELATED COMPOUNDS

[75] Inventor: Carl Peter Krimmel, Wauconda, Ill.

[73] Assignee: G. D. Searle & Co., Chicago, Ill.

[21] Appl. No.: 704,882

[22] Filed: July 13, 1976

Related U.S. Application Data

[63] Continuation-in-part of Ser. No. 622,808, Oct. 16, 1975, abandoned.

[51] Int. Cl.$^2$ .................. C07D 295/10; C07D 243/08; C07D 241/02
[52] U.S. Cl. .......................... 260/239 BC; 260/268 R; 260/268 B; 260/268 H
[58] Field of Search ......... 260/268 B, 268 R, 239 BC, 260/268 H

[56] References Cited
PUBLICATIONS

Paul L. H. Terry et al., Chemical Abstracts, vol. 77, p. 178, (1972).
Roth et al., Archiv der Pharmazie 303, 886, (1970).

*Primary Examiner*—Raymond V. Rush
*Assistant Examiner*—Jose Tovar
*Attorney, Agent, or Firm*—John J. Kolano

[57] ABSTRACT

3,4-bis(4-substituted piperazinyl)-3-cyclobutene-1,2-diones and related compounds having antiviral activity are described herein. The subject compounds can be prepared by reacting 3,4-dimethoxy-3-cyclobutene-1,2-dione with the appropriate substituted piperazine.

13 Claims, No Drawings

3,4-BIS(4-SUBSTITUTED PIPERAZINYL)-3-CYCLOBUTENE-1,2-DIONES AND RELATED COMPOUNDS

The present application is a continuation-in-part of application Ser. No. 622,808, filed Oct. 16, 1975 now abandoned.

The present invention relates to a group of 3,4-bis(4-substituted piperazinyl)-3-cyclobutene-1,2-diones and related compounds. More particularly, the present invention relates to a group of compounds having the following general formula

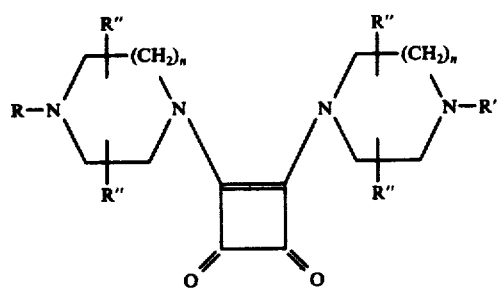

wherein R and R' are the same or different and are alkyl radicals containing 1 to 15 carbon atoms; R" is hydrogen or methyl; and $n$ is one or two. The alkyl groups referred to above are exemplified by methyl, ethyl, propyl, isopropyl, butyl, isobutyl, sec.-butyl, tert.-butyl, pentyl, neopentyl, hexyl, isohexyl, heptyl, and like monovalent saturated acyclic, straight or branched-chain hydrocarbon groups of the formula $$C_nH_{2n+1}$$

wherein $n$ is an integer from 1 to 15.

Equivalent to the compounds of formula (I) for the purposes of this invention are the pharmaceutically acceptable acid addition and quaternary ammonium salts thereof. Such acid addition salts can be derived from a variety of organic and inorganic acids, such as sulfuric, phosphoric, hydrochloric, hydrobromic, hydroiodic, sulfamic, citric, lactic, oleic, succinic, tartaric, cinnamic, acetic, benzoic, gluconic, ascorbic and related acis. Similarly, the quaternary ammonium salts can be derived from a variety of organic esters of sulfuric, hydrohalic and aromatic sulfonic acids. Among such esters are methyl chloride and bromide, ethyl chloride, propyl chloride, butyl chloride, isobutyl chloride, benzyl chloride and bromide, phenethyl bromide, naphthylmethyl chloride, dimethyl sulfate, methyl benzenesulfonate, ethyl toluenesulfonate, ethylene chlorohydrin, propylene chlorohydrin, allyl bromide, methallyl bromide and crotyl bromide.

The compounds of this invention are useful because of their pharmacological properties. In particular, they possess activity as anti-viral agents. Thus, they are effective against viruses such as Influenza A (strain 575) and Herpes hominis type 2. The present compounds can thus be combined with various known excipients and adjuvants in the form of dusts, solutions, suspensions, ointments and sprays to provide compositions useful for disinfecting purposes, such as for laboratory equipment.

The anti-viral utility of the instant compounds is evident from the results of a standardized test for their capacity to inhibit the growth of Influenza A (strain 575). In this test, cell cultures of primary Rhesus monkey kidney maintained in 25 ml. plastic flasks and each containing test compound in concentrations of 625, 125, 25, 5, or 1 μg./ml. are prepared in pairs. These flasks, and an identical pair of flasks containing no test compound, are each inoculated with a dose of influenza virus type A (strain 575) previously shown to produce maximum hemadsorption and minimum cytopathogenic effects after a 24 hour incubation. Where the cultures contain test compound, the virus is added one hour after addition of the compound to the culture. After 24 hour incubation of the cultures, the supernatant fluids are removed and 3.0 ml. of a 0.4% suspension of guinea pig erythrocytes is added to each flask. The flasks are then incubated at 4° C.in a horizontal position for 30 minutes. The flasks are rocked every 10 minutes during the incubation period. After this incubation, the red cell suspension is decanted from each flask, the flasks are washed twice with 3.0 ml. of phosphate buffer solution (pH 7.4) to remove unadsorbed red cells, and 3.0 ml. of distilled water is then added to lyse the absorbed cells. The flasks are further incubated at 37° C. for 30 minutes in a horizontal position and rocked every 10 minutes. After this incubation, the fluid contents of the pairs of flasks are combined to form an assay unit and are placed at room temperature for 15 to 30 minutes to allow settling of cellular debris. A pair of control flasks identical with the above, except for the absence of test compound and virus inoculation, is run concurrently. The resulting hemoglobin solutions from each assay unit are read for optical density in a Beckman Spectrophotometer at about 415 millimicrons. A test compound is considered active if, at one of the tested levels, it reduces the optical density reading by at least 50%, relative to the virus control. Among the compounds of this invention which have been found active in this test are the representative compounds, 3,4-bis(4-pentadecyl-1-piperazinyl-3-cyclobutene-1,2-dione, 3,4-bis(4-propyl-1-piperazinyl)-3-cyclobutene-1,2-dione, and 3,4-bis(4-propyl-1-homopiperazinyl)-3-cyclobutene-1,2-dione.

A further test demonstrating the anti-viral utility of the present compounds is as follows:

The test compound is dissolved in water or a suitable organic solvent. One-quarter inch filter paper discs are impregnated with a test compound solution of a concentration of 0.02 ml./disc and allowed to dry.

Monolayer cell cultures of primary rabbit kidney are established in multi-dish plates, each plate consisting of 6×34 mm. wells. After cell outgrowth, the nutrient fluids are removed from the wells and the cell sheets are inoculated with 0.25 ml. of a dilution of Herpesvirus hominis type 2 strain MS previously shown to cause confluent lysis of the cell sheets. After the virus adsorption period, the inoculum is removed by aspiration, and 2.0 ml. of an agar overlay containing neutral red is added and allowed to solidify. the one-quarter inch filter paper discs previously impregnated with the test compound are then placed onto the center of the agar surface of each well. The plates are incubated at 37° C. for 4 days, at the end of which time they are examined for zones of cytotoxicity and antiviral inhibition. A ratio is then determined for the diameter of the antiviral zone versus the diameter of the cytotoxic zone.

A representative compound of this invention which shows activity in this test is 3-(4-ethyl-1-piperazinyl)-4-(4-propyl-1-piperazinyl)-3-cyclobutene-1,2-dione.

Those skilled in the art will recognize thatobservations of activity and standardized tests for particular biological effects are fundamental to the development of valuable drugs, both veterinary and human.

The compounds of the present invention wherein R and R' are alike are conveniently prepared by contacting 3,4-dimethoxy-3-cyclobutene-1,2-dione of the formula

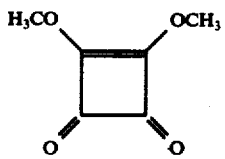

(II)

with two equivalents of the appropriate 1-substituted piperazine of the formula

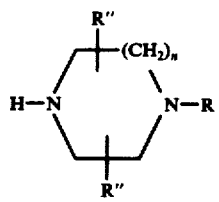

(III)

wherein R, R" and n are defined as above, in a polar, protic solvent.

Suitable solvents include, but are not limited to, methanol, ethanol, 2-propanol, tert.-butyl alcohol and 1-butanol. A particularly preferred solvent for use in the present invention is absolute ethanol.

Time and temperature are not critical factors for the conduct of the reaction, typical times varying from 2–24 hours, and typical temperatures being in the range of room temperature to reflux. Generally, a shorter reaction time is required when the reaction is run at a higher temperature.

The compounds of the present invention wherein R and R' are not alike are conveniently prepared in a stepwise manner by first contacting 3,4-dimethoxy-3-cyclobutene-1,2-dione of formula (II) with one equivalent of one of the appropriate substituted piperazines of formula (III) in a non-polar, aprotic solvent to form a 3-(4-substituted piperazinyl)-4-methoxy-3-cyclobutene-1,2-dione of the formula

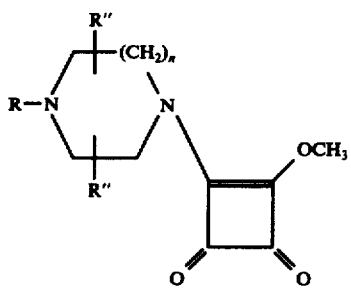

(IV)

wherein R, R" and n are defined as above.

Suitable solvents include, but are not limited to, ethyl ether, tetrahydrofuran, and dioxane. A particularly preferred solvent for use in the present invention is ethyl ether.

Likewise, time and temperature are not critical factors for the conduct of this reaction, a particularly convenient temperature being room temperature, and a preferred time being in the range of 2–4 hours.

The resulting 3-(4-substituted piperazinyl)-4-methoxy-3-cyclobutene-1,2-dione of formula (IV) is then reacted with the desired 1-substituted piperazine of the formula (III) in a polar, protic solvent to give the desired compound of formula (I). This second step is conducted under conditions identical to that of the preparation of the compounds wherein R and R' are alike.

The 3,4-dimethoxy-3-cyclobutene-1,2-dione starting material of formula (II) is conveniently prepared by forming the silver salt of squaric acid with silver nitrate, and refluxing this salt with methyl iodide.

The 1-substituted piperazine starting materials of formula (III) are conveniently prepared by first reacting an appropriate 1-alkanol with mesyl chloride to give the appropriate methylsulfonate ester. This methylsulfonate ester is then reacted with 1-ethoxycarbonylpiperazine in the presence of an acid acceptor to give a 1-ethoxycarbonyl-4-alkyl-piperazine of the formula

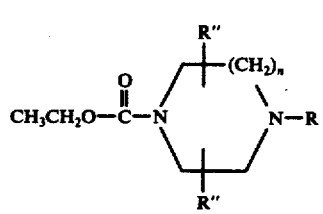

(V)

wherein R, R" and n are defined as above.

Suitable solvents include, but are not limited to, methanol, ethanol, and 2-propanol. A particularly preferred solvent for use in the present invention is ethanol.

The 1-ethoxycarbonyl-4-alkylpiperazine is then reacted with a suitable strong acid to remove the ethoxycarbonyl group and give the desired 1-alkylpiperazine. Suitable strong acids include concentrated sulfuric and concentrated hydrochloric acids with a particularly preferred strong acid being hydrochloric acid.

The following examples describe in detail compounds illustrative of the present invention and methods which have been devised for their preparation. It will be apparent to those skilled in the art that many modifications, both of materials and methods, may be practiced without departing from the purpose and intent of this disclosure. Throughout the examples hereinafter set forth, temperatures are indicated in degrees centigrade (° C.), quantities by weight are indicated in grams and quantities by volume are indicated in milliliters.

PREPARATION OF STARTING MATERIALS

EXAMPLE A

To a cooled solution of 158.3 grams of 1-decanol in 1.0 liter of collidine is added dropwise 126 grams of mesyl chloride. The resulting mixture is stirred at room temperature for 1.5 hours and then poured onto ice. The reaction mixture is extracted with ether and the ether extracts are washed with 10% hydrochloric acid. The ether extracts are combined, dried over anhydrous sodium sulfate, and the solvent removed under reduced pressure to leave an oil which solidifies upon cooling. The oil is dissolved in n-hexane and cooled to yield as crystals, decyl methylsulfonate.

77.3 Grams of decyl methylsulfonate, 44.64 grams of 1-ethoxycarbonylpiperazine, 500 ml. of ethanol, and 39 grams of potassium carbonate are combined and refluxed for approximately 44 hours under a nitrogen atmosphere. After cooling to room temperature the residue is dissolved in a mixture of water and ethyl ether. The organic layer is separated, washed three times with portions of water and dried over anhydrous sodium sulfate. The solvents are removed under reduced pressure to give 1-ethoxycarbonyl-4-decylpiperazine.

53.4 Grams of 1-ethoxycarbonyl-4-decylpiperazine is combined with 300 ml. of concentrated hydrochloric acid and refluxed with stirring under a nitrogen atmosphere for approximately 48 hours. After cooling to room terperature the solvents are removed under reduced pressure. The resulting solid is suspended in ethanol, filtered, and air-dried to yield 1-decylpiperazine.

EXAMPLE B

Substitution of an equivalent quantity of 1-pentadecanol for the 1-decanol used in Example A and repetition of the procedures detailed in paragraph 1 of Example A affords pentadecyl methylsulfonate.

25.0 Grams of 1-ethoxycarbonylpiperazine, 43.0 grams of pentadecyl methylsulfonate, 250 ml. of ethanol, and 9.53 grams of sodium carbonate are combined and heated to gentle reflux. After refluxing for 6 hours, the mixture if filtered, and the solvents removed under reduced pressure. The residue is dissolved in a mixture of water and ethyl ether. The organic layer is separated, washed once with water, and dried over anhydrous magnesium sulfate and anhydrous sodium sulfate. The solvent is removed under reduced pressure to give 1-ethoxycarbonyl-4-pentadecylpiperazine.

To 30.0 grams of 1-ethoxycarbonyl-4-pentadecylpiperazine is added 200 ml. of concentrated hydrochloric acid and the mixture refluxed for 48 hours. The mixture is cooled to approximately 0° C. and the resultant solid filtered and suction-dried. The solid is suspended in water and 10 ml. of 50% sodium hydroxide added. The solution is then extracted with ethyl ether. Removal of the ethyl ether leaves, as an oil, 1-pentadecylpiperazine.

EXAMPLE C

To a solution of 100 grams of squaric acid in 5 liters of water is added 1.4 liters of 1 N sodium hydroxide to bring the solution to a pH of about 7.0. The solution is then treated with 294 grams of silver nitrate to afford a yellow solid which is filtered, washed with acetone, and dried. This solid is then suspended in one liter of anhydrous ethyl ether and 415 ml. of methyl iodide is added. After refluxing 6 hours, the by-product silver iodide is removed by filtration. Concentration of the filtrate and washings under a nitrogen stream yields 3,4-dimethoxy-3-cyclobutene-1,2-dione.

EXAMPLE D

To a suspension of 5.0 grams of 3,4-dimethoxy-3-cyclobutene-1,2-dione in 50 ml. of anhydrous ethyl ether is added a solution of 5.2 grams of 1-methylpiperazine in 50 ml. of anhydrous ethyl ether. The reaction mixture is stirred at room temperature for 2.5 hours under an atmosphere of dry nitrogen. The resulting mixture is cooled and concentrated. It is then filtered, washed and anhydrous ethyl ether and air-dried. The filtered solid is dissolved in ethyl acetate and the insoluble material removed by filtration. The product is recovered from the filtrate as white crystals which are washed with anhydrous ethyl ether and air-dried. The product, 3-(4-methyl-1-piperazinyl)-4-methoxy-3-cyclobutene-1,2-dione, darkens at 262° C. and remains unmelted at 308° C.

EXAMPLE E

Substitution of an equivalent quantity of 1-ethylpiperazine for the 1-methylpiperazine used in Example D and repetition of the procedure detailed therein, affords, as white crystalline needles, 3-(4-ethyl-1-piperazinyl)-4-methoxy-3-cyclobutene-1,2-dione. The crystals turn brown at 260° C. and change to a semi-solid at 299.5° C. to 308° C.

EXAMPLE F

To a solution of 50 grams of cis-2,6-dimethylpiperazine in 130 ml. of water and containing bromphenol blue as indicator is added, with stirring and cooling, a solution of 100 ml. of concentrated hydrochloric acid in 500 ml. of water until the bromphenol blue just turns yellow. Then, 47.7 grams of ethyl chloroformate is introduced in 5 ml. portions of rapid, dropwise addition with stirring. After each 5 ml. addition, aqueous 25% sodium hydroxide solution is added dropwise until the indicator turns green. The addition of reactants is continued until thin layer chromatography shows that all of the piperazine has reacted. The reaction mixture is then made alkaline with aqueous 50% sodium hydroxide solution and then extracted with ethyl ether. The combined ether extracts are dried over anhydrous sodium sulfate and then chromatographed to give 1-ethoxycarbonyl-cis-3,5-dimethylpiperazine.

A mixture of 25.8 grams of 1-ethoxycarbonyl-cis-3,5-dimethylpiperazine, 38.6 grams of propyl 4-toluenesulfonate, 90 ml. of absolute ethanol and 9.5 grams of sodium carbonate is stirred and heated to reflux. After 30 minutes of reflux, vigorous evolution of carbon dioxide begins and continues for about 5 hours. Refluxing is continued for a total of 22 hours. The reaction mixture is then cooled and filtered and the solvent is evaporated. The resulting residue is mixed with 300 ml. of aqueous 1 N sodium hydroxide solution and the mixture is extracted with ethyl ether. The ether extract is washed successively with 100 ml. of aqueous 1 N sodium hydroxide and 100 ml. of water and then dried over anhydrous sodium sulfate. The organic solution is then treated with charcoal and the solvent is evaporated to leave a residue which is purified by chromatography to give 4-ethoxycarbonyl-cis-2,6-dimethyl-1-propylpiperazine.

A mixture of 11 grams of 4-ethoxycarbonyl-cis-2,6-dimethyl-1-propylpiperazine and 150 ml. of concentrated hydrochloric acid is refluxed for 26 hours. The reaction mixture is then cooled and made alkaline by the cautious addition of aqueous 50% potassium carbonate solution. Solid potassium carbonate is then added until a white flocculent precipitate forms. The resulting mixture is extracted with ether and the ether extract is treated with activated carbon and dried over anhydrous sodium sulfate. Evaporation of the solvent on a steam bath under nitrogen leaves a pale orangebrown liquid which is pure cis-2,6-dimethyl-1-propylpiperazine as shown by thin layer chromatography.

ILLUSTRATIONS OF THE INVENTION

EXAMPLE 1

A solution of 1.0 gram of 3,4-dimethoxy-3-cyclobutene-1,2-dione dissolved in 30 ml. of absolute ethanol is mixed with a solution of 1.4 grams of 1-methylpiperazine in 30 ml. of absolute ethanol. The resulting mixture is stirred and heated to reflux for 5 hours under an atmosphere of dry nitrogen. After concentration to approximately one-sixth the volume under reduced pressure, the reaction mixture is cooled and crystallization is induced by scratching. The resultant precipitate is filtered, washed with 0.5 ml. of absolute ethanol, and dried in a steam cabinet. The resulting, product, 3,4-bis(4-methyl-1-piperazinyl)-3-cyclobutene-1,2-dione is obtained as white crystals melting at about 189°-191° C.

EXAMPLE 2

To a stirred, refluxing solution of 0.6 gram of 3,4-dimethoxy-3-cyclobutene-1,2-dione in 20 ml. of absolute ethanol is added dropwise a solution of 1.8 grams of 1-ethylpiperazine and 20 ml. of absolute ethanol. The resulting solution is stirred overnight under a nitrogen atmosphere at room temperature. The reaction mixture is then concentrated under reduced pressure, cooled, and the resultant crystals filtered and dried to afford, as a white solid, 3,4-bis(4-ethyl-1-piperazinyl)-3-cyclobutene-1,2-dione. This compound melts at about 164°-166° C., and is represented by the following structural formula.

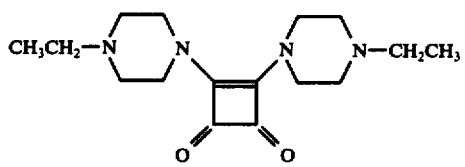

EXAMPLE 3

Substitution of an equivalent quantity of 1-propylpiperazine for the 4-methylpiperazine used in Example 1 and repetition of the procedure detailed therein, affords, as cream colored crystals melting at about 135°-136° C., 3,4-bis-(4-propyl-1-piperazinyl)-3-cyclobutene-1,2-dione.

EXAMPLE 4

To a solution of 0.9 grams of 3,4-dimethoxy-3-cyclobutene-1,2-dione dissolved in 10 ml. of absolute ethanol is added 1.8 grams of 1-butylpiperazine in 5 ml. of absolute ethanol. The reaction mixture is stirred overnight at room temperature under a nitrogen atmosphere. Then, the solvent is removed with a nitrogen stream, 5 ml. of anhydrous ethyl ether is added, and the resultant solid is filtered, washed with ethyl ether, and dried in air. The resulting product, 3,4-bis(4-butyl-1-piperazinyl)-3-cyclobutene-1,2-dione is obtained as white crystals melting at approximately 137.5°-139° C.

EXAMPLE 5

When the procedure of Example 4 is repeated using an equivalent quantity of 1-decylpiperazine for the 1-butylpiperazine used in Example 4, there is obtained 3,4-bis-(4-decyl-1-piperazinyl)-3-cyclobutene-1,2-dione, as white crystals melting at about 122°-124° C. This compound is represented by the following structural formula.

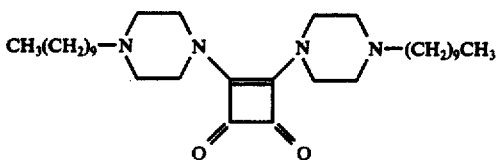

EXAMPLE 6

To a solution of 1.4 grams of 3,4-dimethoxy-3-cyclobutene1,2-dione in 15 ml. of absolute ethanol is added a solution of 5.9 grams of 1-pentadecylpiperazine in 15 ml. of absolute ethanol. The resulting mixture is stirred overnight at room temperature under a nitrogen atmosphere. The resulting precipitate is then filtered, washed with 1.0 ml. of absolute ethanol, and air-dried. It is then purified by elution from a silica gel column using 99% methylene chloride plus 1% ammonium hydroxide, followed by 1% ethanol-98% methylene chloride plus 1% ammonium hydroxide. The pure fractions are combined and suspended in anhydrous ethyl ether, filtered, and air-dried to give white crystalline flakes. The resulting product 3,4-bis(4-pentadecyl-1-piperazinyl)-3-cyclobutene-1,2-dione melts at about 99°-101.5° C., and is represented by the following structural formula.

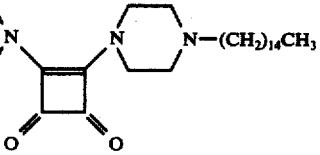

EXAMPLE 7

To a stirred, refluxing solution of 2.2 grams of 3-(4-ethyl-1-piperazinyl)-4-methoxy-3-cyclobutene-1,2-dione dissolved in 30 ml. of absolute ethanol under an atmosphere of dry nitrogen, is added a solution of 1.0 gram of 1-methylpiperazine in 30 ml. of absolute ethanol. The resulting mixture is refluxed for 4 hours and then stripped of solvent under reduced pressure until the volume is approximately 15 ml. The concentrate is treated with decolorizing charcoal and filtered through a bed of diatomaceous earth. Crystallization is induced in the filtrate and the resulting crystalline precipitate is filtered, washed with absolute ethanol, and dried in a steam cabinet. The resulting product, 3-(4-ethyl-1-piperazinyl)-4-(4-methyl-1-piperazinyl)-3-cyclobutene-1,2-dione, is obtained as white crystals melting at about 166.5-169° C. This product is represented by the following structural formula.

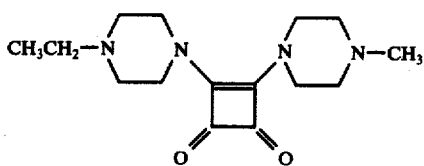

EXAMPLE 8

Substitution of an equivalent quantity of 1-propylpiperazine for the methylpiperazine used Example 7, and substantial repetition of the procedure detailed therein, affords 3-(4-ethyl-1-piperazinyl)-4-(4-propyl-1-piperazinyl)-3-cyclobutene-1,2-dione. This compound melts at approximately 134°–135° C., and is represented by the following structural formula.

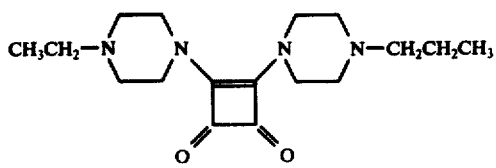

EXAMPLE 9

To a solution of 2.1 grams of 3-(4-methyl-1-piperazinyl)-4-methoxy-3-cyclobutene-1,2-dione in 25 ml. of methanol is added a solution of 1.4 grams of 1-butylpiperazine in 5 ml. of methanol at room temperature. The resulting mixture is stirred overnight and filtered to remove turbidity. The solvent is removed by drying with a nitrogen stream and 10 ml. of anhydrous ethyl ether is added. The resulting solid is filtered, washed with anhydrous ethyl ether, and air-dried. The product, 3-(4-butyl-1-piperazinyl)-4-(4-methyl-1-piperazinyl)-3-cyclobutene1,2-dione was shown to be essentially pure by thin layer chromatography. The compound was obtained as white crystals melting at about 119.5°–135° C.

EXAMPLE 10

To a solution of 0.5 grams of 3,4-bis(4-ethyl-1-piperazinyl)-3-cyclobutene-1,2-dione in 50 ml. of 2-butanone is added 5 ml. of methyl iodide. The reaction mixture is allowed to stand for approximately 2 hours. The resultant yellow precipitate is then filtered, washed with 2-butanone and dried in vacuo at 50° C. The resulting product, 3,4-bis(4-ethyl-1-piperazinyl)-3-cyclobutene-1,2-dione dimethiodide is obtained as pale yellow crystals that darken at 250.5° C. and melt and decompose with gas evolution at 256°–265° C. This product is represented by the following structural formula.

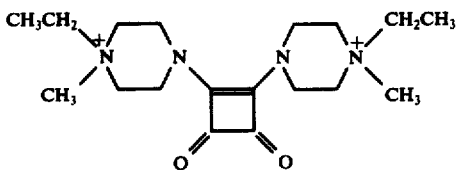

EXAMPLE 11

A solution of 3.1 grams of 1-propylhomopiperazine in 20 ml. of methanol is mixed with a solution of 1.6 grams of 3,4-dimethoxy-3-cyclobutene-1,2-dione in 50 ml. of methanol and refluxed under nitrogen for 5 hours. The methanol solvent is evaporated by heating on a steam bath and the residual solid is dissolved in 70 ml. of anhydrous benzene at room temperature, treated with charcoal, and filtered. The resulting filtrate is diluted with 250 ml. of hexane and the precipitate which forms is separated by filtration and dried and then recrystallized from 1000 ml. of refluxing hexane to give 3,4-bis(4-propyl-1-homopiperazinyl)-3-cyclobutene-1,2-dione as white crystals melting at about 90°–92° C.

EXAMPLE 12

A solution of 1.5 grams of 2,6-dimethyl-1-propylpiperazine in 10 ml. of methanol is mixed with a solution of 3,4-dimethoxy-3-cyclobutene-1,2-dione in 25 ml. of methanol and refluxed for 5 hours. The solvent is then evaporated by heating on a steam bath and the resulting red semi-crystalline residue is triturated with anhydrous ethyl ether and filtered and the filter cake is washed with 5 ml. of anhydrous ethyl ether to remove the colored by-products and leave 3,4-bis(3,5-dimethyl-4-propyl-1-piperazinyl)-3-cyclobutene-1,2-dione as a grey-white crystalline solid melting at about 145°–147° C.

What is claimed is:

1. A compound of the formula

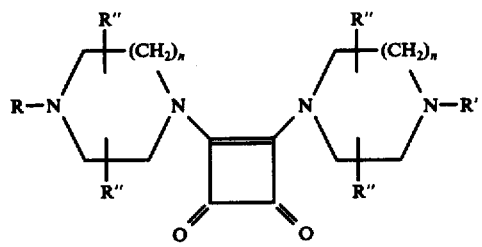

wherein R and R' are the same or different and are alkyl radicals having 1 to 15 carbon atoms; R'' is hydrogen or methyl; and n is one or two.

2. A compound according to claim 1 having the formula

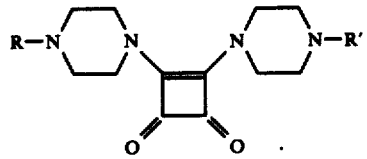

wherein R and R' are the same of different and are alkyl having 1 to 15 carbon atoms.

3. A compound according to claim 1 which is 3-(4-ethyl-1-piperazinyl)-4-(4-methyl-1-piperazinyl)-3-cyclobutene-1,2-dione.

4. A compound according to claim 1 which is 3-(4-ethyl-1-piperazinyl)-4-(4-propyl-1-piperazinyl)-3-cyclobutene-1,2-dione.

5. A compound according to claim 1 which is 3-(4-butyl-1-piperazinyl)-4-(4-methyl-1-piperazinyl)-3-cyclobutene-1,2-dione.

6. A compound according to claim 1 of the formula

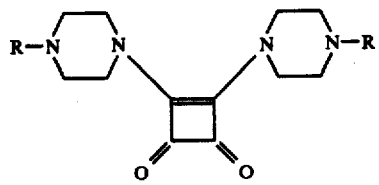

wherein R is alkyl having 1 to 15 carbon atoms.

7. A compound according to claim 1 which is 3,4-bis(4-ethyl-1-piperazinyl)-3-cyclobutene-1,2-dione.

8. A compound according to claim 1 which is 3,4-bis(4-propyl-1-piperazinyl)-3-cyclobutene-1,2-dione.

9. A compound according to claim 1 which is 3,4-bis(4-butyl-1-piperazinyl)-3-cyclobutene-1,2-dione.

10. A compound according to claim 1 which is 3,4-bis(4-decyl-1-piperazinyl)-3-cyclobutene-1,2-dione.

11. A compound according to claim 1 which is 3,4-bis(-b 4-pentadecyl-1-piperazinyl)-3-cyclobutene-1,2-dione.

12. A compound according to claim 1 which is 3,4-bis(4-propyl-1-homopiperazinyl)-3-cyclobutene-1,2-dione.

13. A compound according to claim 1 which is 3,4-bis(3,5-dimethyl-4-propyl-1-piperazinyl)-3-cyclobutene-1,2-dione.

* * * * *